(12) United States Patent
Bordy (10) Patent No.: US 10,418,399 B2
(45) Date of Patent: Sep. 17, 2019

(54) LENS-FREE IMAGING SYSTEM COMPRISING A DIODE, A DIAPHRAGM, AND A DIFFUSER BETWEEN THE DIODE AND THE DIAPHRAGM

(71) Applicant: Commissariat à l'énergie atomique et aux énergies alternatives, Paris (FR)

(72) Inventor: Thomas Bordy, Grenoble (FR)

(73) Assignee: COMMISSARIAT À L'ÉNERGIE ATOMIQUE ET AUX ÉNERGIES ALTERNATIVES, Paris (FR)

(*) Notice: Subject to any disclaimer, the term of this patent is extended or adjusted under 35 U.S.C. 154(b) by 165 days.

(21) Appl. No.: 15/528,055

(22) PCT Filed: Nov. 9, 2015

(86) PCT No.: PCT/EP2015/076016
§ 371 (c)(1),
(2) Date: May 18, 2017

(87) PCT Pub. No.: WO2016/078946
PCT Pub. Date: May 26, 2016

(65) Prior Publication Data
US 2017/0317125 A1 Nov. 2, 2017

(30) Foreign Application Priority Data
Nov. 21, 2014 (FR) .................... 14 61316

(51) Int. Cl.
| H01L 27/146 | (2006.01) |
| G01N 15/14 | (2006.01) |
| G01N 21/47 | (2006.01) |
| G01N 21/51 | (2006.01) |
| G03H 1/04 | (2006.01) |
| G02B 21/00 | (2006.01) |

(52) U.S. Cl.
CPC ... H01L 27/14625 (2013.01); G01N 15/1434 (2013.01); G01N 15/1468 (2013.01);
(Continued)

(58) Field of Classification Search
CPC .......... G01N 15/1434; G01N 15/1468; G01N 21/4788; H01L 27/14625; H01L 27/14643
(Continued)

(56) References Cited

U.S. PATENT DOCUMENTS 8,842,901 B2 * 9/2014 Ozcan ............... G06K 9/0014
382/133
2007/0263914 A1 11/2007 Tibbetts
(Continued)

OTHER PUBLICATIONS

International Search Report for PCT/EP2015/076016, dated Jan. 25, 2016.
(Continued)

*Primary Examiner* — Que Tan Le
(74) *Attorney, Agent, or Firm* — B. Aaron Schulman, Esq.; Stites & Harbison, PLLC (57) ABSTRACT

This lensless imaging system comprises a receiving support configured to receive a sample, a light source configured to emit a light beam illuminating the sample in an illumination direction, the light source including a diode and a diaphragm, the diaphragm being positioned between the diode and the receiving support in the lighting direction, and a matrix photodetector configured to acquire at least one image of the sample, each image being formed by radiation emitted by the illuminated sample and including at least one elementary diffraction pattern, the receiving support being positioned between the light source and the matrix photodetector in the illumination direction.
The system further comprises a light diffuser positioned between the diode and the diaphragm.

15 Claims, 6 Drawing Sheets

(52) U.S. Cl.
CPC ......... *G01N 21/4788* (2013.01); *G01N 21/51* (2013.01); *G02B 21/0008* (2013.01); *G03H 1/0443* (2013.01); *H01L 27/14643* (2013.01); *G01N 2015/1454* (2013.01); *G02B 21/0088* (2013.01); *G03H 2001/0447* (2013.01)

(58) Field of Classification Search
USPC ...................................................... 250/208.1
See application file for complete search history.

(56) References Cited

U.S. PATENT DOCUMENTS

| | | |
|---|---|---|
| 2011/0136165 A1 | 6/2011 | Vojnovic et al. |
| 2015/0281609 A1 | 10/2015 | Poher et al. |

OTHER PUBLICATIONS

Petruck P et al: "Optimized coherence, parameters for high-resolution holographic, microscopy", Applied Physics B ; Lasers and Optics, Springer, Berlin, DE, vol. 106, No. 2, Nov. 11, 2011(Nov. 11, 2011), pp. 339-348, XP035010548, ISSN: 1432-0649, DOI: 10.1007/S00340-011-4787-6 figure 1, 1 Introduction pp. 339-340, 2 Experimental setup and methods pp. 340-341.

Kesavan Srikanth Vinjimore et al: "Real-time label-free detection of dividing cells by means of lensfree video-microscopy", Journal of Biomedical Optics, SPIE—International Society for Optical Engineering, US, vol. 19, No. 3,Mar. 5, 2014(Mar. 5, 2014), p. 36004, XP060047341, ISSN: 1083-3668, DOI: 10.1117/1.JB0.19.3.036004 [retrieved on Mar. 5, 2014] figure 1 2.1 Lensfree Video-Microscopy.

* cited by examiner

(PRIOR ART)

LENS-FREE IMAGING SYSTEM COMPRISING A DIODE, A DIAPHRAGM, AND A DIFFUSER BETWEEN THE DIODE AND THE DIAPHRAGM

FIELD OF THE INVENTION

The present invention relates to a lensless imaging system, also called lens-free imaging system. The lensless imaging system comprises a receiving support configured to receive a sample, and a light source configured to emit a light beam for illuminating the sample in an illumination direction, the light source including a diode and a diaphragm, the diaphragm being positioned between the diode and the receiving support in the illumination direction.

The lensless imaging system also comprises a matrix photodetector configured to acquire at least one image of the sample, each image being formed by radiation emitted by the illuminated sample and including at least one elementary diffraction pattern, the receiving support being positioned between the light source and the matrix photodetector in the illumination direction.

The invention relates to lensless imaging, also called contact imaging, i.e., the acquisition, by the matrix photodetector, of images formed by the radiation directly emitted by the sample, with no magnifying lens positioned between the sample and the matrix photodetector. In this case, the matrix photodetector is also called a lensless imaging device, and is able to form an image of the sample while being placed at a small distance therefrom. A small distance refers to a distance comprised between 100 µm and several centimeters, preferably less than 1 cm.

BACKGROUND OF THE INVENTION

An imaging system of the aforementioned type is known from document EP 2,122,326 B1. The imaging system comprises a light source suitable for illuminating a sample and a CCD sensor able to acquire at least one image of the illuminated sample. The light source includes a light-emitting diode with an opening diameter equal to 60 µm, or a light-emitting diode with a large zone associated with a diaphragm, also called pinhole, having a diameter equal to 6 µm. The observed diffraction patterns then include a center and one or several concentric rings positioned around the center.

However, the diffraction patterns observed with such an imaging system are not optimal; in particular, when the surface of the diode is too large, the diaphragm projects the image of the electrode(s) making up the light-emitting diode on the sensor. Thus, when no sample is present, the image collected on the sensor is not homogenous.

This effect occurs in the presence of a sample, which is detrimental to the quality of the obtained images.

SUMMARY OF THE INVENTION

The aim of the invention is therefore to propose an imaging system making it possible to resolve this problem.

To that end, the invention relates to a lensless imaging system of the aforementioned type, wherein the system further comprises a light diffuser positioned between the diode and the diaphragm.

According to other advantageous aspects of the invention, the lensless imaging system comprises one or more of the following features, considered alone or according to all technically possible combinations:

the diode is a light-emitting diode;

the diode is a laser diode, such as a VCSEL laser diode;

the light diffuser has a diffusion angle, and the diffusion angle is greater than or equal to 5°, preferably greater than or equal to 20°, still more preferably greater than or equal to 30°;

the diffusion angle verifies the following equation:

$$\beta = \sqrt{\alpha^2 + \Delta^2}$$

where $\Delta$ represents the diffusion angle of the light diffuser, $\alpha$ represents a divergence angle of the diode, and $\beta$ represents a resultant diffusion angle at the output of the light diffuser;

the diode has a divergence angle, the light diffuser has a diffusion angle, and the value of the divergence angle is smaller than the value of the diffusion angle;

the light diffuser includes a smooth surface and a diffusing surface, and the diffusing surface is positioned away from the diaphragm;

the light diffuser is made from a material chosen from the group consisting of: a polyester, a polycarbonate and an acrylic material;

the diaphragm has a diameter with a value comprised between 50 µm and 500 µm, preferably substantially equal to 150 µm;

the distance between the support and the diaphragm in the illumination direction is comprised between 1 cm and 30 cm, preferably comprised between 1 cm and 10 cm, still more preferably substantially equal to 5 cm; and the distance between the support and the matrix photodetector in the illumination direction is less than or equal to 1 cm, and preferably less than 5 mm.

BRIEF DESCRIPTION OF THE DRAWINGS

These features and advantages of the invention will appear upon reading the following description, provided solely as a non-limiting example, and done in reference to the appended drawings, in which.

DETAILED DESCRIPTION OF PREFERRED EMBODIMENTS

Conventionally, in the present description, the expression "substantially equal to" will express a relationship of equality to within plus or minus 10%, preferably to within plus or minus 5%.

Figure 1:
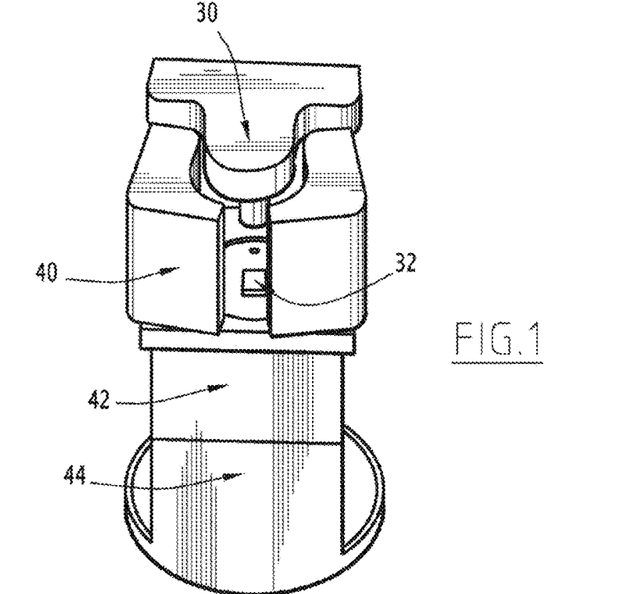
FIG. 1 is a perspective view of a lensless imaging system according to the invention.
Figure 2:
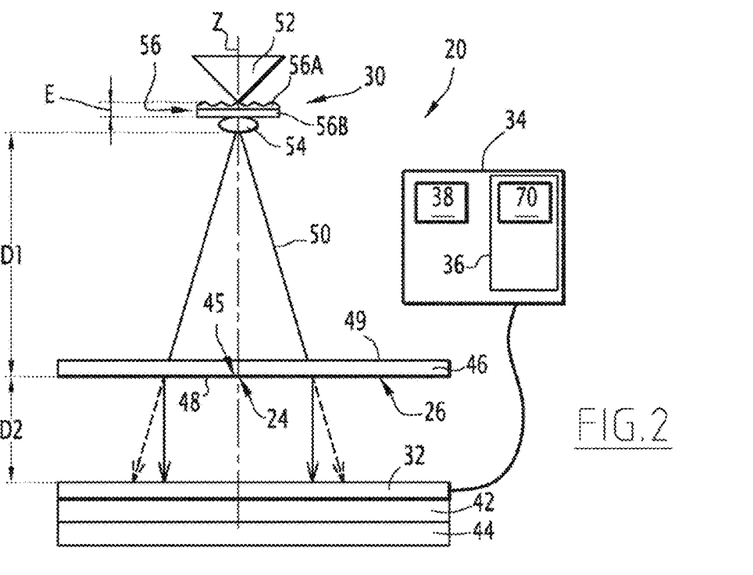
FIG. 2 is a very schematic illustration of the imaging system of FIG. 1, comprising a light source able to illuminate a sample and a matrix photodetector able to establish a diffraction pattern emitted by the illuminated sample, the light source including a diode, a diaphragm and a light diffuser positioned between the diode and the diaphragm.

In FIGS. 1 and 2, an imaging system 20 for a sample 24 comprises a receiving support 26 suitable for receiving the sample 24. The imaging system 20 also comprises a light source 30 and a matrix photodetector 32 suitable for acquiring several successive images of a ray emitted by the sample 24 illuminated by the light source 30.

The imaging system 20 is generally suitable for acquiring one or several images of the sample 24 using a lensless imaging methodology, the matrix photodetector 32 not including a magnification lens.

The imaging system 20 also comprises an information processing unit 34, shown in FIG. 2, comprising a memory 36 and a processor 38 associated with the memory 36.

As an optional addition, the imaging system 20 comprises a device 40 with swinging doors, the doors being painted black, making it possible to isolate the ray emitted by the illuminated sample 24 from the outside environment. The swinging door device 40 makes it possible, when the swinging doors are closed, for a technician to then operate in ambient light, but without disrupting the measurements done inside the imaging system.

The imaging system 20 also comprises a heat dissipater 42 and a fan 44 to regulate the temperature of the matrix photodetector 32, in particular to cool it in case of excessive heating. These elements are optional.

The sample 24 includes particles 45, called diffracting particles in the continuation of the description, each particle 45 being able to create waves diffracted during the illumination of the sample 24.

The sample 24 is for example a liquid, such as a bodily fluid having been removed from the patient beforehand, the withdrawal step not being within the scope of the invention. The sample 24 for example includes cerebrospinal fluid or blood.

The receiving support 26 is positioned between the light source 30 and the matrix photodetector 32, and is substantially perpendicular to a vertical direction Z corresponding to the illumination direction of the sample 24 by the light source 30, as shown in FIG. 2.

The receiving support 26 comprises a transparent slide 48, for example made from glass. In this example, the receiving support 26 is placed at the bottom of a Petri dish 46. The Petri dish 46 here serves to confine the sample 24, and is optional. It is suitable for being placed directly on the matrix photodetector 32. The Petri dish 46 additionally includes a cover 49 in order to protect the sample 24.

The light source 30 is suitable for emitting a light beam 50 in the vertical direction Z in order to illuminate the sample 24 including the diffracting particles 45.

The light source 30 is positioned at a first distance D1 from the transparent slide 48 in the illumination direction, in the example of FIGS. 1 and 2 corresponding to the vertical direction Z. The first distance D1 preferably has a value comprised between 1 cm and 30 cm, preferably comprised between 1 cm and 20 cm, preferably comprised between 1 cm and 10 cm, still more preferably substantially equal to 5 cm. The first distance D1 corresponds to the distance between the light source 30 and the receiving support 26 in the illumination direction, and more specifically to the distance between the diaphragm 54 and the slide 48 in this illumination direction.

The light source 30 is preferably spatially coherent and preferably monochromatic. The term monochromatic designates a spectral width smaller than 80 nm, preferably smaller than 50 nm at mid-height.

The light source 30 includes a diode 52, also called LED (light-emitting diode), and a diaphragm 54, as shown schematically in FIG. 2. The diaphragm 54 is also called pinhole.

According to the invention, the light source 30 further includes a light diffuser 56 positioned between the diode 52 and the diaphragm 54 in the illumination direction.

The matrix photodetector 32 is suitable for acquiring successive images of the ray emitted by the sample 24, containing the diffracting particles 45, illuminated by the light beam 50. Emitted ray refers to the ray passing through the sample 24 such that the matrix photodetector 32 and the light source 30 are situated on either side of the sample 24 including the diffracting particles 45.

The matrix photodetector 32 is a two-dimensional image sensor, i.e., in a plane substantially perpendicular to the vertical axis Z. The matrix photodetector 32 is a pixelated image sensor, for example a CMOS (Complementary Metal Oxide Semiconductor) sensor. Alternatively, the matrix photodetector 32 is a CCD (Charged-Coupled Device) sensor.

The matrix photodetector 32 includes a plurality of pixels, not shown, each having dimensions smaller than or equal to 10 µm, and preferably smaller than 5 µm, and still more preferably smaller than 2 µm.

The matrix photodetector 32 may additionally include micro-lenses, not shown, each micro-lens being positioned above a corresponding pixel. Such micro-lenses are integrated into the sensor and make it possible to improve the collection performance, but without forming a magnifying lens positioned between the receiving support 26 and the photodetector 32.

The images acquired by the matrix photodetector 32 are formed by the ray emitted directly by the illuminated sample 24, in the absence of a magnifying lens positioned between the receiving support 26 and the matrix photodetector 32. The photodetector 32 is also called a lensless imaging device, and is able to form an image of the liquid 24, while being placed at a small distance therefrom. A small distance refers to a distance smaller than several centimeters, preferably smaller than 1 cm. The photodetector 32 is positioned at a second distance D2 from the transparent slide 48 in the illumination direction Z, and the second distance D2 is then smaller than several centimeters, preferably smaller than 1 cm.

Favoring a small value for the second distance D2, i.e., a short distance between the matrix photodetector 30 and the receiving support 26, makes it possible to limit the interference phenomena between different diffraction patterns when the sample 24 is illuminated.

The matrix photodetector 32 is then suitable for acquiring an image of at least one elementary diffraction pattern 60 emitted by the sample 24, each elementary diffraction pattern 60 corresponding to waves diffracted by a diffracting particle 45 when the sample 24 is illuminated. Thus, the matrix photodetector 32 makes it possible to obtain an image $I_n$ including one or several elementary diffraction patterns 60.

Each image $I_n$ acquired by the matrix photodetector 32 includes a plurality of pixels $I_n(x,y)$, each being identified by an x-axis and a y-axis in the image, and the matrix photodetector 32 is suitable for measuring the intensity $I(x,y)$ of each pixel.

The memory 36 is able to store software 70 for processing one or several images of the sample 24.

The processor 38 is suitable for running the processing software 70.

The diffracting particles 45 are for example biological particles, i.e., cells (in particular blood cells, and for example white or red blood cells), bacteria or bacterial colonies, or cell aggregates.

Alternatively, the diffracting particles 45 are microbeads, dust, pollen, or surface asperities of the sample 24.

One skilled in the art will then understand that the imaging system 20 according to the invention is a lensless imaging system, suitable for acquiring an image including one or several elementary diffraction patterns 60, each elementary diffraction pattern 60 corresponding to waves diffracted by a particle 45 during the illumination of the sample 24, irrespective of the type of particle 45, and in general, irrespective of the type of sample 24.

The diffracting particles 45 generally have a diameter smaller than 100 µm. The diameter of the diffracting particles 45 is for example comprised between 1 µm and 100 µm. The cells, such as the white blood cells and red blood cells, have a diameter of approximately 10 µm.

The diode 52 has a divergence angle α. A divergence angle refers to the half-angle of the emission cone of the diode 52.

The diode 52 is for example a light-emitting diode. The light-emitting diode for example has a wavelength substantially equal to 525 nm.

Alternatively, the diode 52 is a laser diode, such as a laser diode of the VSCEL (Vertical Cavity Surface Emitting Laser) type.

The diaphragm 54 for example has a diameter comprised between 50 µm and 500 µm, preferably substantially equal to 150 µm. This makes it possible to increase the spatial coherence of the light radiation.

The light diffuser 56 has a diffusion angle Δ. The value of the diffusion angle Δ is for example greater than or equal to 20°, preferably greater than or equal to 30°, still more preferably greater than or equal to 40°.

The diffusion angle Δ verifies the following equation:

$$\beta = \sqrt{\alpha^2 + \Delta^2} \quad (1)$$

where Δ represents the diffusion angle of the light diffuser 56,

α represents the divergence angle of the diode 52, and

β represents the diffusion angle resulting at the output of the light diffuser 56.

The value of the divergence angle α is preferably smaller than the value of the diffusion angle Δ.

In the illumination direction, the light diffuser 56 has a thickness E with a value comprised between 100 µm and 10 mm, preferably comprised between 500 µm and 2 mm.

The light diffuser 56 is for example in the form of a thin, flexible film, and its thickness is then typically smaller than or equal to 1.5 mm, for example comprised between 0.5 mm and 1 mm. Alternatively, the light diffuser 56 is in the form of a rigid substrate, and its thickness is then typically greater than or equal to 0.5 mm, for example comprised between 2 mm and 3 mm.

The light diffuser 56 is made from a material chosen from the group consisting of: a polyester, a polycarbonate and an acrylic material.

The light diffuser 56 is for example positioned in contact with the diaphragm 54, more specifically in contact with the face of the diaphragm 54 that is oriented toward the diode 52, i.e., in contact with the upper face of the diaphragm 54 in the example of FIGS. 1 and 2. Alternatively, the light diffuser 56 is positioned in contact with the diode 52, more specifically in contact with the face of the diode 52 that is oriented toward the diaphragm 54, i.e., in contact with the lower face of the diaphragm 52 in the example of FIGS. 1 and 2. Also alternatively, the light diffuser 56 is positioned away from the diode 52 and the diaphragm 54.

According to one embodiment, the light diffuser 56 includes a diffusing layer 56A deposited on a substrate 56B, the latter acting as support for the diffusing layer 56A. The substrate 56B forms a smooth surface, and the diffusing layer 56A forms a diffusing surface. In such an embodiment, it has been observed that the diffusing layer 56A is preferably positioned at a distance from the diaphragm 54, and for example at a distance greater than 50 µm, or even greater than 100 µm, from the diaphragm 54 in the illumination direction Z. In other words, the diffusing surface is preferably positioned away from the diaphragm 54.

Figure 9:
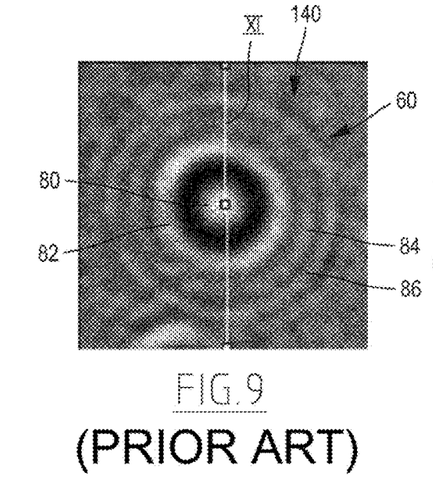
FIG. 9 is a view of a diffraction pattern acquired with the imaging system of the prior art.
Figure 10:
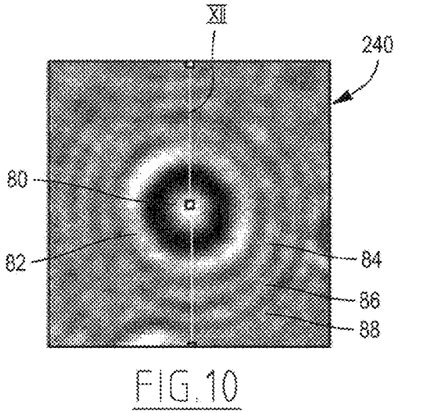
FIG. 10 is a view of a diffraction pattern acquired with the imaging system of FIGS. 1 and 2.

Each elementary diffraction patterns 60 includes a central zone 80, also called center, the intensity of which is substantially homogenous, this central zone 80 being surrounded by concentric rings 82, 84, 86, 88, the intensity of which is alternately low (dark rings) and high (light rings), as shown in FIGS. 9 and 10. The rings 82, 84, 86, 88 respectively corresponds to a first light ring, a second light ring, a third light ring and a fourth light ring.

The processing software 70 forms means for processing the image(s) acquired from the sample 24.

Alternatively, the processing means 70 are made in the form of programmable logic components, or in the form of dedicated integrated circuits.

The processing software 70 is for example suitable for identifying moving elementary diffraction patterns 60 from acquired images $I_n$, $I_{n+1}$, and counting particles 45 moving within the sample 24, from identified moving elementary diffraction patterns.

Additionally or alternatively, the processing software 70 is suitable for characterizing each identified moving elementary diffraction pattern 60, i.e., determining one or several criteria for each of these patterns. Such a criterion is for example a ratio R between the maximum intensity and the median intensity (or the mean intensity) of a region of interest of said diffraction pattern.

The processing software 70 is then able to sort the detected elementary diffraction patterns 60 into at least two separate categories according to the selected characterization criterion, in order to classify the particles corresponding to the detected elementary diffraction patterns into different classes. The classification of said diffraction patterns 60 is for example done by comparing the calculated ratio R with at least one predetermined threshold.

Alternatively, the processing software 70 is suitable for reconstructing optical properties of the sample 24, in particular the absorption or the phase lag, from an image acquired by the matrix photodetector 32.

Alternatively, the processing software 70 is suitable for characterizing a variation in the speed of the particles 45 contained in the sample 24 or for characterizing an agglomeration of said particles 45, in particular when the sample 24 is a liquid sample containing blood, and the particles 45 are blood particles.

One skilled in the art will then understand that the imaging system 20 according to the invention is suitable for any type of application implementing a lensless imaging system, the imaging system 20 according to the invention making it possible to improve the quality of the images acquired by the matrix photodetector 32, as will now be described in light of FIGS. 3 to 22, and irrespective of the type of application.

Figure 3:
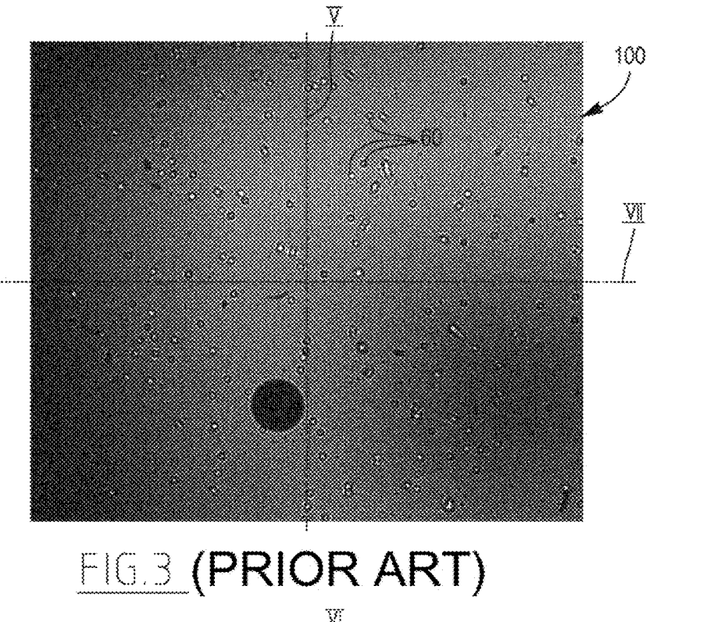
FIG. 3 is a view of a zone of an image acquired with an imaging system of the prior art.

FIG. 3 shows a zone 100 of an image acquired with an imaging system of the prior art, i.e., with an imaging system not including a light diffuser positioned between the diode and the diaphragm in the illumination direction. The zone 100 includes several elementary diffraction patterns 60.

Figure 4:
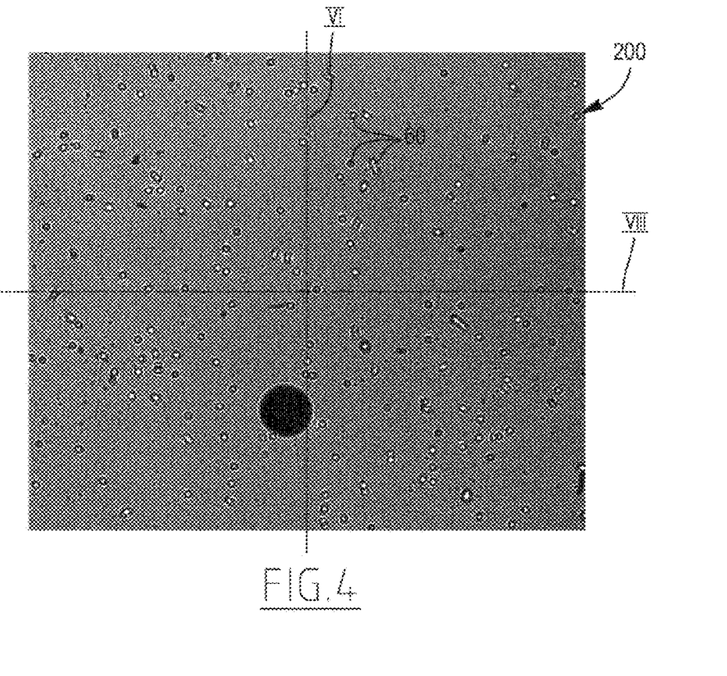
FIG. 4 is a view of a zone of an image acquired with an imaging system of FIGS. 1 and 2.
Figure 5:
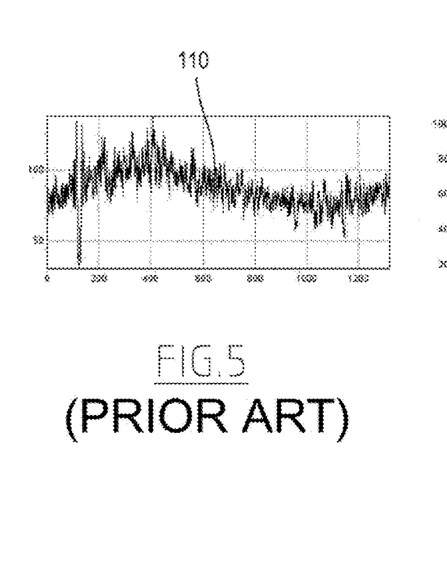
FIG. 5 is an intensity profile of the zone of the image of FIG. 3 along line V.

FIG. 4 shows a zone 200 of an image acquired with an imaging system 20 according to the invention, including the light diffuser 56 positioned between the diode 52 and the diaphragm 54 in the illumination direction. The zone 200 also includes several elementary diffraction patterns 60.

The zone 100 and the zone 200 each correspond to a same portion of the illuminated sample 24, as attested to by the presence of a black disc near the center of each of the zones 100 and 200.

One can then see that the image acquired with the imaging system 20 according to the invention is significantly more homogenous than that acquired with the imaging system of the prior art. Indeed, the zone 100 shows a darkening of its periphery, in particular with the dark corners on the left in FIG. 3, with a rendering similar to vignetting, while the zone 200 does not have such darkening of its periphery. Furthermore, the zone 100 has darkening in its central part, this darkening not being perceptible in the zone 200.

This is confirmed by FIGS. 5 to 8, which each show an intensity profile along a respective line V to VIII of FIGS. 3 and 4. Each profile is an intensity profile expressed in gray level based on a distance expressed in μm. The profiles corresponding to the imaging system of the prior art are profiles 110 and 120, shown in FIGS. 5 and 7, along lines V and VII of FIG. 3, respectively. The profile 110 along line V is also called vertical profile, and the profile 120 along line VII is also called horizontal profile.

Figure 6:
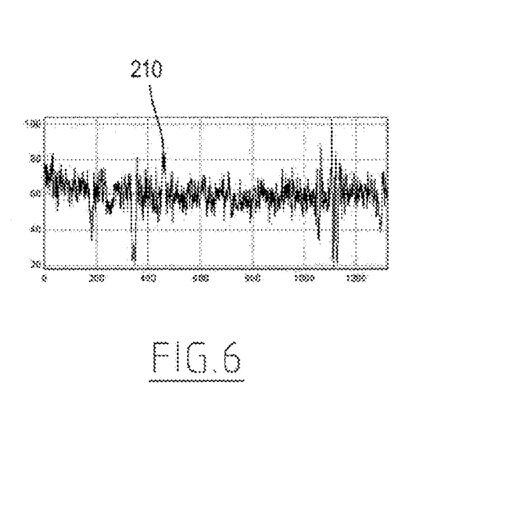
FIG. 6 is an intensity profile of the zone of the image of FIG. 4 along line VI.
Figure 7:
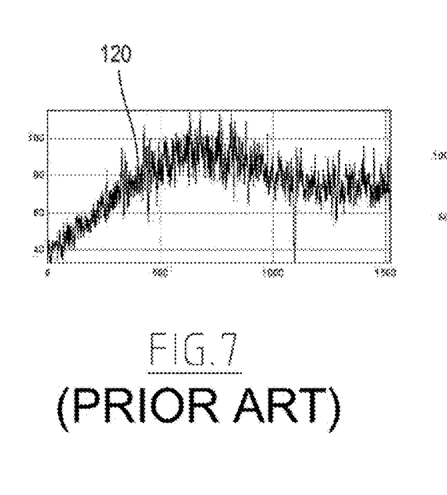
FIG. 7 is a view similar to that of FIG. 5, along line VII.
Figure 8:
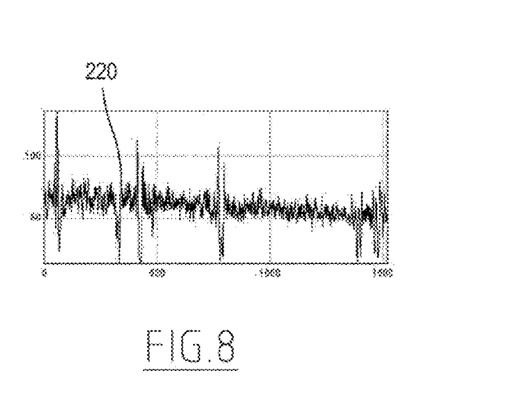
FIG. 8 is a view similar to that of FIG. 6, along line VIII.

The profiles corresponding to the imaging system 20 according to the invention are profiles 210 and 220, shown in FIGS. 6 and 8, along lines VI and VIII of FIG. 4, respectively. Similarly, the profile 210 along line VI is also called vertical profile, and the profile 220 along line VIII is also called horizontal profile.

One skilled in the art will then see that the profiles 210 and 220 obtained with the imaging system 20 according to the invention each have, aside from a few periodic peaks, a low intensity variation in gray level, the mean value being close to the value 50 each time. Conversely, the profiles 110 and 120, obtained with the imaging system of the prior art, have, aside from a few periodic peaks, a high intensity variation, the intensity varying between about 50 and 130 for the vertical profile 110 and between about 20 and 120 for the vertical profile 120.

Furthermore, the imaging system 20 according to the invention makes it possible to have a better resolution of the diffraction rings 82, 84, 86, 88, as will be explained now in light of FIGS. 9 to 12. Indeed, the diffraction pattern shown in FIG. 10 has a higher contrast than that shown in FIG. 9.

Additionally, the imaging system 20 according to the invention is more robust with respect to an offset of the position of the light source 30 relative to the central axis of the diaphragm 54. The insertion of the diffuser 56 between the light source 30 and the diaphragm 54 makes the imaging system 20 more tolerant of such an offset.

FIG. 9 shows a zone of interest 140 of an image acquired with the imaging system of the prior art, this zone of interest 140 including a corresponding elementary diffraction pattern 60 with its center 80 and its rings 82, 84, 86. FIG. 10 shows a similar zone of interest 240 of an image acquired with the imaging system 20 according to the invention, this zone of interest 240 also including a corresponding elementary diffraction pattern 60 with its center 80 and its rings 82, 84, 86, 88.

A visual comparison of FIGS. 9 and 10 then shows much better visibility of the diffraction rings 82, 84, 86, 88 in the image acquired with the imaging system 20 according to the invention than that acquired with the imaging system of the prior art. In other words, the rings 82, 84, 86, 88 stand out much more clearly, or have a better resolution, in the image acquired using the imaging system 20 according to the invention.

Figure 11:
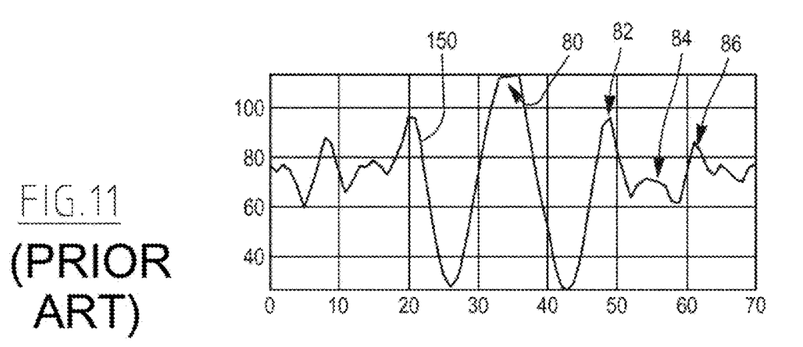
FIG. 11 is an intensity profile of the image of FIG. 9 along line XI.
Figure 12:
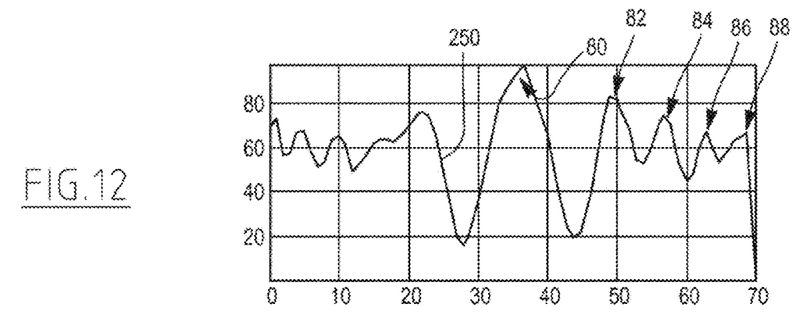
FIG. 12 is an intensity profile of the image of FIG. 10 along line XII.

This visual perception is confirmed by FIGS. 11 and 12, respectively showing a vertical profile 150 along line XI of FIG. 9, obtained with the imaging system of the prior art, and a vertical profile 250 along line XII of FIG. 10, obtained with the imaging system 20 according to the invention. The comparison of the vertical profiles 150 and 250 then clearly shows that the second light ring 84, as well as the following light rings 86, 88, correspond to more distinct intensity peaks on the vertical profile 250 obtained with the imaging system 20 according to the invention than on the vertical profile 150 obtained with the imaging system of the prior art.

The imaging system 20 according to the invention then makes it possible to reduce, or even avoid, a loss of resolution on the rings 82, 84, 86, 88 of the elementary diffraction patterns 60.

As previously described, the invention relates to any light diffuser 56 positioned between the diode 52 and the diaphragm 54 in the illumination direction.

The inventors have further observed that the obtained results are even better for certain values of the diffusion angle Δ of the light diffuser 56, as will be described below in light of FIGS. 13 to 22.

Figure 13:
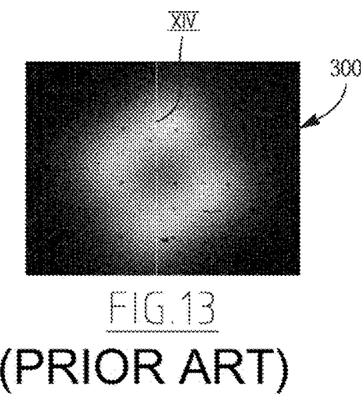
FIG. 13 is a view of an image acquired with the matrix photodetector of the imaging system of the prior art.
Figure 14:
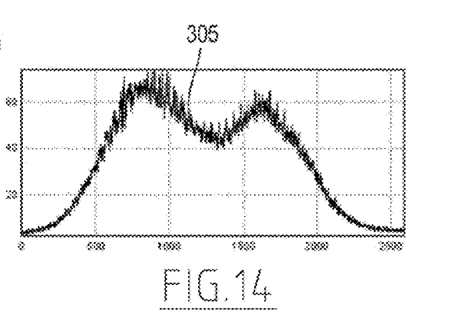
FIG. 14 is an intensity profile of the image of FIG. 13 along line XIV.

FIG. 13 shows an image 300 acquired with the imaging system of the prior art, and FIG. 14 shows the corresponding vertical intensity profile 305 along line XIV.

Figure 15:
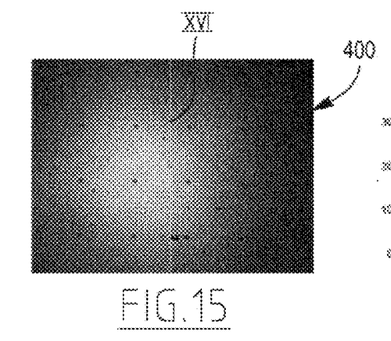
FIGS. 15, 17, 19, 21 are respective views of an image acquired with the imaging system of FIGS. 1 and 2, for different values of a diffusion angle of the light diffuser, and FIGS. 16, 18, 20 and 22, respectively, are each an intensity profile of the image of FIGS. 15, 17, 19 and 21, respectively, along lines XVI, XVIII, XX and XXII, respectively.
Figure 16:
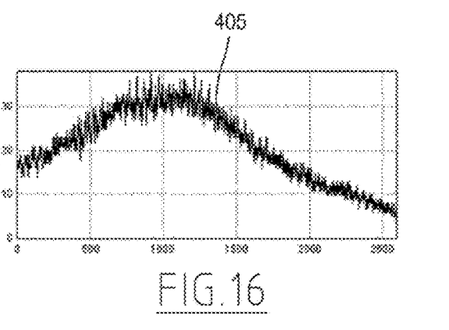
Figure 17:
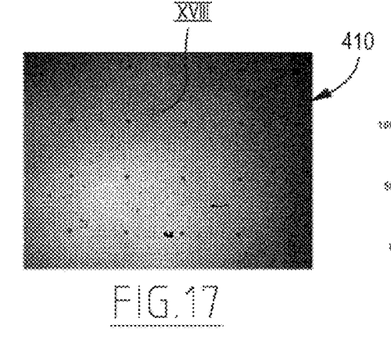
Figure 18:
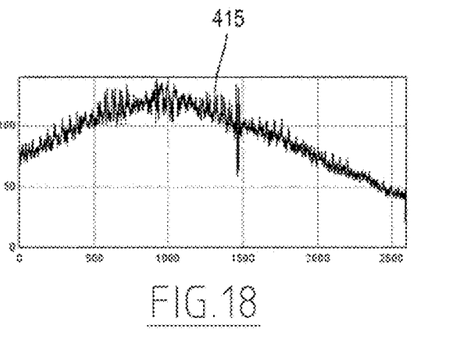
Figure 19:
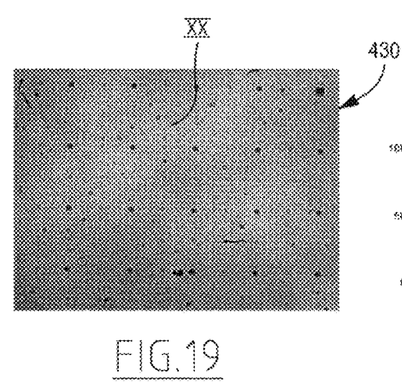
Figure 20:
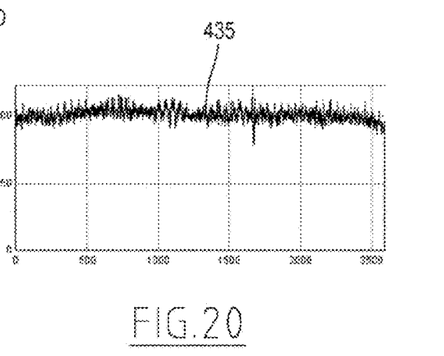
Figure 21:
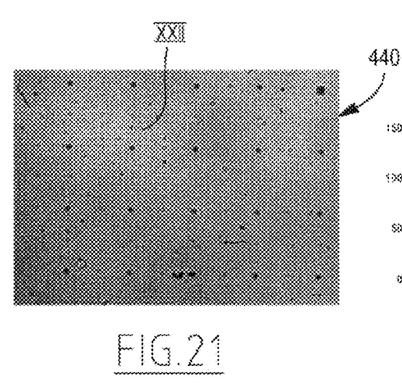
Figure 22:
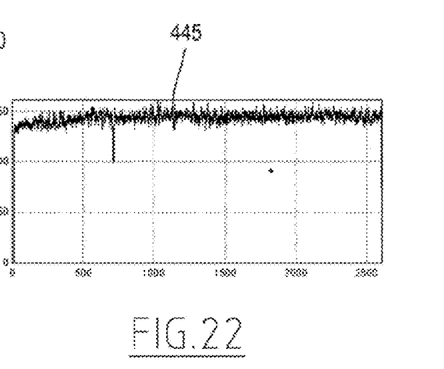

FIGS. 15, 17, 19 and 21 each show an image 400, 410, 430, 440 acquired by the imaging system 20 according to the invention, for increasing values of the diffusion angle Δ, FIG. 15 corresponding to a value substantially equal to 5° of the diffusion angle Δ, FIG. 17 corresponding to a value substantially equal to 10° of said diffusion angle Δ, FIG. 19 corresponding to a value substantially equal to 40° of said diffusion angle Δ, and FIG. 21 corresponding to a value substantially equal to 60° of said diffusion angle Δ. FIGS. 16, 18, 20 and 22 respectively show the corresponding vertical intensity profiles 405, 415, 435, 445 along lines XVI, XVIII, XX and XXII, respectively, of FIGS. 15, 17, 19 and 21.

In the example of FIGS. 13, 15, 17, 19 and 21, the transparent slide 48 has points each defining a test pattern. These points appear in FIGS. 13, 15, 17, 19 and 21, as well as in FIGS. 3 and 4.

One can then see that the darkening of the periphery of the acquired image is most pronounced with the imaging system of the prior art corresponding to image 300, and that the mere addition of the light diffuser 56, even with a low value of the diffusion angle Δ like in the case of image 400 with a diffusion angle Δ substantially equal to 5°, makes it possible to reduce this darkening of the periphery of the acquired image. This can also be observed through the profiles 405, 415, 435 and 445 obtained with the imaging system 20 according to the invention, which have less significant intensity variations than for the profile 305 obtained with the imaging system of the prior art.

One can further see that the entire acquired image has a quasi-uniform intensity once the value of the diffusion angle Δ is greater than or equal to 20°, in particular greater than or equal to 30°, as illustrated by the profiles 435 and 445, respectively, having an intensity value substantially equal to 100 in gray level, and 150 in gray level, respectively.

One can thus see that the imaging system 20 according to the invention makes it possible to improve the image(s) acquired by the matrix photodetector 32, in particular to have diffraction patterns 60 with more visible diffraction rings 82, 84, 86, 88.

The invention claimed is:

1. A lensless imaging system, comprising:
   a receiving support configured to receive a sample,
   a light source configured to emit a light beam for illuminating the sample in an illumination direction, the light source including a diode and a diaphragm, the diaphragm being positioned between the diode and the receiving support in the illumination direction,
   a matrix photodetector configured to acquire at least one image of the sample, each image being formed by a radiation emitted by the illuminated sample and including at least one elementary diffraction pattern, the receiving support being positioned between the light source and the matrix photodetector in the illumination direction,
   wherein the system further comprises a light diffuser positioned between the diode and the diaphragm, said light diffuser including a diffusing layer deposited on a substrate, said diffusing layer being positioned at a distance from the diaphragm, the light diffuser having a diffusion angle, and the value of the diffusion angle being greater than or equal to 30°.

2. The system according to claim 1, wherein the diode is a light-emitting diode.

3. The system according to claim 1, wherein the diode is a laser diode.

4. The system according to claim 1, wherein the diffusion angle verifies the following equation:

$$\beta = \sqrt{\alpha^2 + \Delta^2}$$

where Δ represents the diffusion angle of the light diffuser,
α represents a divergence angle of the diode, and
β represents a diffusion angle resulting at the output of the light diffuser.

5. The system according to claim 1, wherein the diode has a divergence angle, and the value of the divergence angle is smaller than the value of the diffusion angle.

6. The system according to claim 1, wherein the substrate forms a smooth surface and the diffusing layer forms a diffusing surface.

7. The system according to claim 1, wherein the light diffuser is made from a material chosen from the group consisting of: a polyester, a polycarbonate and an acrylic material.

8. The system according to claim 1, wherein the diaphragm has a diameter with a value comprised between 50 μm and 500 μm.

9. The system according claim 1, wherein the distance between the support and the diaphragm in the illumination direction is comprised between 1 cm and 30 cm.

10. The system according to claim 1, wherein the distance between the support and the matrix photodetector in the illumination direction is less than or equal to 1 cm.

11. The system according to claim 3, wherein the laser diode is a VCSEL laser diode.

12. The system according to claim 8, wherein the diaphragm has a diameter with a value substantially equal to 150 μm.

13. The system according to claim 9, wherein the distance between the support and the diaphragm in the illumination direction is comprised between 1 cm and 10 cm.

14. The system according to claim 13, wherein the distance between the support and the diaphragm in the illumination direction is substantially equal to 5 cm.

15. The system according to claim 10, wherein the distance between the support and the matrix photodetector in the illumination direction is less than 5 mm.

* * * * *